(12) United States Patent
Bäck

(10) Patent No.: US 7,828,785 B2
(45) Date of Patent: Nov. 9, 2010

(54) BELTED ABSORBENT GARMENT AND METHOD FOR MAKING AND TESTING

(75) Inventor: Lucas Bäck, Billdal (SE)

(73) Assignee: SCA Hygiene Products AB, Gothenburg (SE)

(*) Notice: Subject to any disclaimer, the term of this patent is extended or adjusted under 35 U.S.C. 154(b) by 73 days.

(21) Appl. No.: 12/371,757

(22) Filed: Feb. 16, 2009

(65) Prior Publication Data

US 2009/0157028 A1 Jun. 18, 2009

Related U.S. Application Data

(63) Continuation of application No. PCT/SE2006/001087, filed on Sep. 25, 2006.

(51) Int. Cl.
A61F 13/15 (2006.01)
(52) U.S. Cl. .................... 604/392; 604/394; 604/396
(58) Field of Classification Search ............. 604/392, 604/394, 396
See application file for complete search history.

(56) References Cited

U.S. PATENT DOCUMENTS

| 5,226,992 | A | 7/1993 | Morman | |
|---|---|---|---|---|
| 5,376,430 | A | 12/1994 | Swenson et al. | |
| H1674 | H | * 8/1997 | Ames et al. | 604/389 |
| 5,669,897 | A | 9/1997 | Lavon et al. | |
| 2003/0109843 | A1 | 6/2003 | Gibbs | |
| 2005/0027279 | A1 | 2/2005 | Minato et al. | |
| 2005/0131373 | A1 | 6/2005 | Wright et al. | |
| 2006/0004339 | A1 | 1/2006 | Lord et al. | |

FOREIGN PATENT DOCUMENTS

| EP | 0 287 388 A2 | 10/1988 |
|---|---|---|
| EP | 0 409 307 A2 | 1/1991 |
| EP | 0 487 758 A1 | 6/1992 |
| EP | 0 605 012 A1 | 7/1994 |
| EP | 0 641 522 A1 | 9/1994 |

(Continued)

OTHER PUBLICATIONS

Form PCT/ISA/210 (International Search Report) dated Apr. 18, 2007.

(Continued)

Primary Examiner—Jacqueline F. Stephens
(74) Attorney, Agent, or Firm—Buchanan Ingersoll & Rooney PC

(57) ABSTRACT

An absorbent garment having belt sections attached to the waist portion of a first body panel and fastened together by a first fastener, a second body panel at its waist portion being provided with a second fastener adapted to be fastened to at least one of the belt sections; wherein when the absorbent garment is tested by: (a) fastening a belted absorbent garment around movable mechanical members which are adapted to mechanically simulate a user's waist or hips; and (b) moving said members away from each other using actuating members and moving them back to their initial position so as to simulate the expansion and contraction of a user's waist as he/she moves; the garment does not slip down more than 15 cm from its initial position during at least ten expansion/contraction cycles of the test apparatus and for at least 30 seconds.

20 Claims, 12 Drawing Sheets

FOREIGN PATENT DOCUMENTS

| | | |
|---|---|---|
| EP | 0 646 062 B1 | 8/1996 |
| EP | 1 384 457 A1 | 1/2004 |
| FR | 2 586 558 A1 | 3/1987 |
| GB | 2 244 422 A | 12/1991 |
| GB | 2 292 067 A | 2/1996 |
| GB | 2 389 665 A | 12/2003 |
| JP | 3471999 B2 | 12/2003 |
| WO | WO 98/29251 A1 | 7/1998 |
| WO | WO 03/000165 A1 | 1/2003 |
| WO | WO 03/047488 A1 | 6/2003 |
| WO | WO 2006/065175 A1 | 6/2006 |
| WO | WO 2007/071267 A1 | 6/2007 |
| WO | WO 2008/039112 A1 | 4/2008 |
| WO | WO 2008/143560 A1 | 11/2008 |

OTHER PUBLICATIONS

Form PCT/ISA/237 (Written Opinion of the International Searching Authority) dated Apr. 18, 2007.
Form PCT/IPEA/408 (Written Opinion of the International Preliminary Examining Authority) dated Sep. 11, 2008.

* cited by examiner

BELTED ABSORBENT GARMENT AND METHOD FOR MAKING AND TESTING

CROSS-REFERENCE TO RELATED APPLICATIONS

The present application is a continuation of PCT/SE 2006/001087, filed on Sep. 28, 2006, the entire contents of which is incorporated herein by reference.

TECHNICAL FIELD

The present invention concerns an absorbent garment, such as a diaper or an incontinence guard, for an adult or a child, which comprises a belt as part of the fastening means for attaching the absorbent garment around the waist of a user. The present invention also concerns a method for manufacturing and testing such a belted absorbent garment.

BACKGROUND

A belted absorbent garment usually comprises a front body panel adapted to be applied over the stomach of a user, a back body panel adapted to be applied over the back of the user and a crotch portion adapted to extend over the crotch of the user between his/her legs. The belted absorbent garment further comprises opposed laterally extending belt sections attached to the waist portion of the back body panel. The belt sections are adapted to be wrapped around the waist of the user of the garment and are fastened together after which the front body panel is fastened to the external surface of the belt in such a way that the garment will assume a pant-like shape. Examples of belted absorbent garments may for example be found in European patent applications no. EP-A-0287388, EP-A-0409307, EP-A-0605012 and French patent application no. FR-A-2586558.

As a user moves about (i.e. eats, breathes, sneezes, walks etc.), the circumference of the user's waist expands and contracts, which consequently results in the belt sections being strained and relaxed. Repeated or exaggerated expansion and contraction of the belt sections can lead to permanent deformation of the belt sections and thus result in the length of the belt being irreversibly increased, which in turn may result in the absorbent garment slipping down from the user's waist and, in the worst case, falling off the user.

It is known to provide an absorbent garment with a belt made entirely of elastic material, however elastic material is generally more expensive than inelastic material, it is much more difficult to attach fastening means, such as hooks, to an elastic material and an elastic belt is not as easy for a user to handle as an inelastic belt. Absorbent garments comprising partly elastic belts, whereby a belt is provided with at least one elastic panel, are also known, for example through Japanese patent no. JP-B-3471999 and European patent no. EP-B-0487758. However known belted absorbent garments have a tendency to slip down from a user's waist if subjected to repeated or exaggerated expansion and contraction.

When a user purchases a belted absorbent garment it is not possible for him/her to predict how well the belt of the absorbent garment will maintain its original circumference when in use and consequently how well the belted absorbent garment will stay in place since test methods according to the prior art do not provide such information. Only test specimens cut from the fabrics that constitute a belted absorbent garment are tested in known test methods.

British patent no. GB 2389665, for example, discloses a method for determining the stretch and recovery characteristics of fabrics, in particular stretch fabrics. The method comprises the steps of mounting a fabric test piece into a clamping frame and mounting the clamping frame together with its fabric test piece in a stretching device. The fabric is deformed by flexing it a pre-determined number of times at a pre-determined speed. The patent further discloses equipment for simulating the stretch and recovery characteristics of fabrics during their normal use. The equipment comprises a clamping device to retain and support a test piece of fabric, a hemispherical block beside which the fabric is positioned and a geared motor and crank arrangement to move the hemispherical block laterally in order to stretch the fabric. A fabric test piece may be repeatedly stretched and relaxed a predetermined number of times, as would occur in actual user use.

U.S. Pat. No. 4,366,814 discloses an elastic bandage material. 1-inch wide strips of test material are mounted in the jaws of an Instron tensile tester and stretched to the desired percent elongation. The strip is then allowed to recover by decreasing the distance through which it has been stretched.

A disadvantage with testing only a test specimen of fabric is that a belted absorbent garment usually comprises several different parts comprising various materials, which are used to fasten the belted absorbent garment around a user's waist, such as adhesive tape, elasticated sections, elastic panels and other attached or integrated belt elements. It is therefore difficult to determine the net elastic and tensile properties of all of said parts/materials from an analysis of each part/material separately. Furthermore, the weight of a belted absorbent garment and its contents are not taken into account in the tests carried out on a test specimen, even though the weight of a belted absorbent garment and its contents will influence how well the belted absorbent garment stays in place on a user.

OBJECT AND SUMMARY

An object of the present invention is to provide an improved belted absorbent garment, the belted absorbent garment having improved fit, comfort and the capability of staying in place on the user during normal use of the garment.

This object is achieved by a belted absorbent garment having a longitudinal and a transverse direction and comprising a first body panel, a second body panel and a crotch portion therebetween, each of said first and second body panels having a waist portion. Said absorbent garment further being provided with belt sections attached to the waist portion of a first body panel and being adapted to be wrapped around the waist of the user of the garment and fastened together by means of first fastening means. The second body panel at its waist portion being provided with second fastening means adapted to be fastened to the belt sections in such a way that the garment will assume a pant-like shape. When tested on a Cyclic Waist Expansion Test apparatus as described below, the absorbent garment does not slip down more than 15 cm from its initial position on the Cyclic Waist Expansion Test apparatus during at least ten expansion/contraction cycles of the Cyclic Waist Expansion Test and during at least 30 seconds after being subjected to at least ten expansion/contraction cycles of the Cyclic Waist Expansion Test. Such a belted absorbent garment is not only comfortable to wear and easy to fasten and handle but also provides a good fit and stays reliably in place during use even if its user is very active.

According to an embodiment of the invention the absorbent garment does not slip down more than 10 cm and most preferably not more than 7 cm from its initial position on the Cyclic Waist Expansion Test apparatus described herein. A graded scale of how well an absorbent garment stays on the Cyclic Waist Expansion Test apparatus can therefore be defined by how much said absorbent garment slips down from its initial position during and after being subjected to at least ten expansion/contraction cycles of the Cyclic Waist Expansion Test.

According to an embodiment of the invention the belt sections have a longitudinal and a transverse direction and at least one belt section comprises at least one elastic panel that extends up to 25% of the length of the belt section in the transverse direction of the absorbent garment as measured in the initial non-elongated state of the belt section.

A belt section of the absorbent garment therefore comprises an inelastic part and, optionally, at least one elastic panel that is arranged to be capable of being elongated in a substantially transverse direction of the absorbent garment, whereby the expressions "elastic" and "inelastic" are defined using the elasticity test described below. In the case where a belt section of the absorbent garment comprises one or more elastic panels, it or they extend(s) over no more than 25% of the total belt section length in the transverse direction thereof, preferably over no more than 15% of the total belt section length and most preferably no more than 10% of the total belt section length.

Furthermore, said at least one elastic panel is easy to stretch, i.e. it requires a force no greater than 15 N to elongate it by at least 60% according to the elasticity test described below.

Elasticity Test

The elasticity test measures how an elastic material behaves during repeated load and unload cycles. The test sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The test sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

Crosshead speed: 500 mm/min

Clamp distance: 50 mm

Preload: 0.05 N

The test sample is placed in the clamps according to the marks and it is made sure that the test sample is centred and fastened perpendicularly in the clamps. The tensile tester is started and three cycles between 0 and the predetermined elongation, equal to the highest defined first load, are performed. Before the last cycle, the test sample is relaxed for one minute, then the permanent elongation is measured by stretching the test sample until a force of 0.1 N is detected and the elongation is read.

An elastic material is defined as a material having a permanent elongation after relaxation of less than 10% after the material has been subjected to an elongation of 30% in the aforementioned elasticity test. An elongation of 30% means an elongation to a length that is 30% longer than the initial length of the sample. An inelastic material has a permanent elongation after relaxation of more than 10% after having been subjected to an elongation of 30%.

According to an embodiment of the invention said at least one elastic panel comprises any elastic material, an elastic film, an elastic non-woven or an elastic laminate, such as a stretch activated laminate, known in the art. The elastic laminate may be a laminate between two or more non-woven layers, two or more film layers or a combination of film and non-woven layers. One group of elastic laminates are so called "stretch-bonded" laminates, in which the elastic layer is stretched in at least one direction before laminating it with one or more inelastic layers. After the tension is removed from the elastic layer it can freely retract to its un-tensioned state, and the inelastic layer(s) laminated thereto become gathered, giving a three-dimensional puckering.

Another group of elastic laminates are so called "neck bonded" laminates, which refer to laminates in which an elastic material is bonded to a non-elastic material while the non-elastic member is extended under conditions reducing its width or "necked". "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO 03/047488, in which inelastic non-woven layers are laminated to an elastic film layer, and the laminate is stretched above the point of failure of the non-woven materials, so that the inelastic layers break. Inelastic non-woven layers may also be laminated to an un-stretched elastic film layer. The elasticity of the laminate is then activated by mechanical stretching.

Examples of elastic laminates are described in EP-B-0 646 062, WO 98/29251, WO 03/000165 and U.S. Pat. No. 5,226,992. Examples of commercially available elastic laminates are Fabriflex™ 306 from Tredegar and PK 6358 from Nordenia.

According to another embodiment of the invention said at least one elastic panel comprises an elastic laminate, comprising at least one elastic film layer and at least one non-woven layer, in which the layers have been ultrasonically bonded, adhesively bonded, thermo-bonded, extrusion bonded, or bonded using a combination of said bonding methods.

According to another embodiment of the invention the elastic panel comprises one or more elastic strips or threads contractably affixed between web materials, which may be inelastic.

According to a further embodiment of the invention the, or each, elastic panel extends 1-15 cm along the length of the belt section in the transverse direction thereof as measured in the belt section's initial non-elongated state. An elastic panel is usually attached by adhesive, thermo-bonding, ultrasonic or laser welding to the substantially inelastic part of a belt, resulting in an overlap of elastic and substantially inelastic material, whereby the length of said overlap as measured in the transverse direction may be up to 15 mm. All of the dimensions of elastic panels along the length of a belt in the transverse direction of the absorbent garment which are given in this document refer to the active elastic length i.e. the length of the elastic material of the belt, which can be elongated on application of an elongating force in the transverse direction of the absorbent garment and retracted when releasing the force, whereby "elastic material" is as defined according to the aforementioned elasticity test.

According to an embodiment of the invention the belt comprises two belt sections that are connected to opposite sides of the front or back panel of the absorbent garment. According to another embodiment of the invention the two belt sections are interconnected by a waist band extending in the transverse direction along the waist portion of the front or back body panel. The belt sections in this case refer to the sections extending laterally outside the respective body panel.

The total length of the belt of the belted absorbent garments disclosed herein is defined as the total combined length of the belt sections and the width of the body panel to which the belt sections are attached. A "belt section" is defined as a portion of the belt that extends from a peripheral edge of the chassis of an absorbent garment. The width of the body panel is measured in the transverse direction of the absorbent garment in between the peripheral edges of the chassis to which the belt sections are attached. In other words the total length of the belt is the distance between the distal end of one belt section to the distal end of the other belt section as measured in the initial non-elongated state of the belt. Instead of attaching two opposing belt sections to the longitudinal peripheral edges of a body panel, a belt may be attached to the transverse peripheral edge of a body panel whereby a "belt section" in such cases is defined as that part of the belt transversely outside of lines that constitute an imaginary extension of the longitudinal peripheral edges of the body panel.

At least one belt section comprises at least one elastic panel. According to a preferred embodiment of the invention the proximal edge one elastic panel is located within 5 cm, more preferably within 3 cm of the respective longitudinal peripheral edge of the chassis of the absorbent garment or its imaginary extension in the longitudinal direction, on a waistband interconnecting two belt sections. It should be noted that said at least one elastic panel extends along up to 25% of the respective belt section length as measured in the belt section's initial non-elongated state and that this extension refers to the elastic material in the belt sections only and does not include the extension of any elastic material in the body panel to which the belt sections are attached or alternatively in a waistband interconnecting two belt sections. According to an embodiment of the invention, the proximal edge of an elastic panel is arranged in abutment with the respective longitudinal peripheral edge of the body panel. Alternatively an elastic panel may instead, or additionally, be arranged in the waist area of a body panel or in the intermediate waistband interconnecting the belt sections.

According to another embodiment of the invention the length of each belt section in the transverse direction thereof is from 25 to 55 cm as measured in the belt section's initial non-elongated state.

According to a further embodiment of the invention the width of the belt section is from 50 to 160 mm. A medium sized absorbent garment may for example have a belt width of 60-120 mm and a large product may have a belt width of 70-140 mm.

The present invention also concerns a method for determining how well a belted absorbent garment will stay in place around a user's waist when in use.

The method comprises the steps of fastening a belted absorbent garment around movable mechanical members, such as contoured plates, which are intended to mechanically simulate a human user's waist and/or hips (i.e. the belted absorbent garment is not tested on a human being); moving said members away from each other, using actuating means, such as a pneumatic or hydraulic cylinder and piston or magnetic means, and moving them back to their initial position so as to simulate the expansion and contraction of a user's waist as he/she moves. It should be noted that the word "movable" is intended to mean that at least one of said mechanical members is movable with respect to the other mechanical member. For example, if the test equipment consists of two contoured plates, the position of a first contoured plate may be arranged to remain fixed while the second contoured plate is movable with respect to the first.

According to an embodiment of the invention the method comprises the step of repeating said expansion and contraction cycle by moving the movable members away from each other and back to their initial position a plurality of times.

According to an embodiment of the invention the method comprises the steps of positioning a belted absorbent garment in a clearly marked initial position on movable mechanical members and fastening the belted absorbent garment around the movable mechanical members by stretching the belt using a predetermined force. The movable mechanical members are then moved a predetermined distance apart and back at a predetermined speed a predetermined number of times. The final position of the belted absorbent product, measured from its initial position, is recorded a predetermined time after the final expansion and contraction cycle has been completed. It is namely recorded whether the absorbent garment still remains on the movable mechanical members and, if so, it is recorded how far from the marked initial position the absorbent garment has slipped, if at all.

According to another embodiment of the invention the method comprises the step of adding weight to the belted absorbent garment while it is being tested or before testing begins.

According to a further embodiment of the invention the method comprises the step of providing a vertical scale on, or in the vicinity of, said movable mechanical members to determine the amount of downward slippage during the, or each, expansion and contraction cycle.

According to an embodiment of the invention the method comprises the steps of positioning a belted absorbent garment in a clearly marked initial position on movable mechanical members and fastening the belted absorbent garment around the movable mechanical members by stretching the belt using a predetermined force. The method also comprises the steps of wrapping the crotch portion and body panels around the movable mechanical members and fastening the second body panel to the external surface of at least one of the belt sections. According to a preferred embodiment of the invention, the crotch portion and body panels are wrapped around the movable mechanical members while stretching said crotch portion and body panels with a predetermined force. The method further comprises the steps of adding a predetermined weight to the belted absorbent garment, moving the movable mechanical members a predetermined distance apart and back at a predetermined speed a predetermined number of times, and recording the position of the belted absorbent product from its initial position a predetermined time after the final expansion and contraction cycle has been completed. In this embodiment the inventive method is referred to as The Cyclic Waist Expansion Test.

The present invention further concerns a method for manufacturing a belted absorbent garment according to any of the embodiments of the invention and consequently concerns the belted absorbent garments manufactured by said manufacturing method. The manufacturing method comprises the steps of the test method described above according to any of the embodiments of the invention as a quality control measure to ensure that said manufacturing process is working correctly.

According to an embodiment of the invention the method comprises the step of providing a manufactured belted absorbent garment or its packaging with information and/or a parameter that is indicative of how well said belted absorbent garment stays in place on a user's waist when in use. Customers purchasing the belted absorbent garment would therefore be provided with an accurate indication of how well the belt of the absorbent garment will maintain its original circumference when in use and consequently how well the belted absorbent garment may stay in place when in use.

BRIEF DESCRIPTION OF THE DRAWINGS

The embodiments of the present invention will hereinafter be further explained by means of non-limiting examples with reference to the appended figures where.

It should be noted that the drawings have not been drawn to scale and that the dimensions of certain features have been exaggerated for the sake of clarity.

DETAILED DESCRIPTION OF EMBODIMENTS

Figure 1:
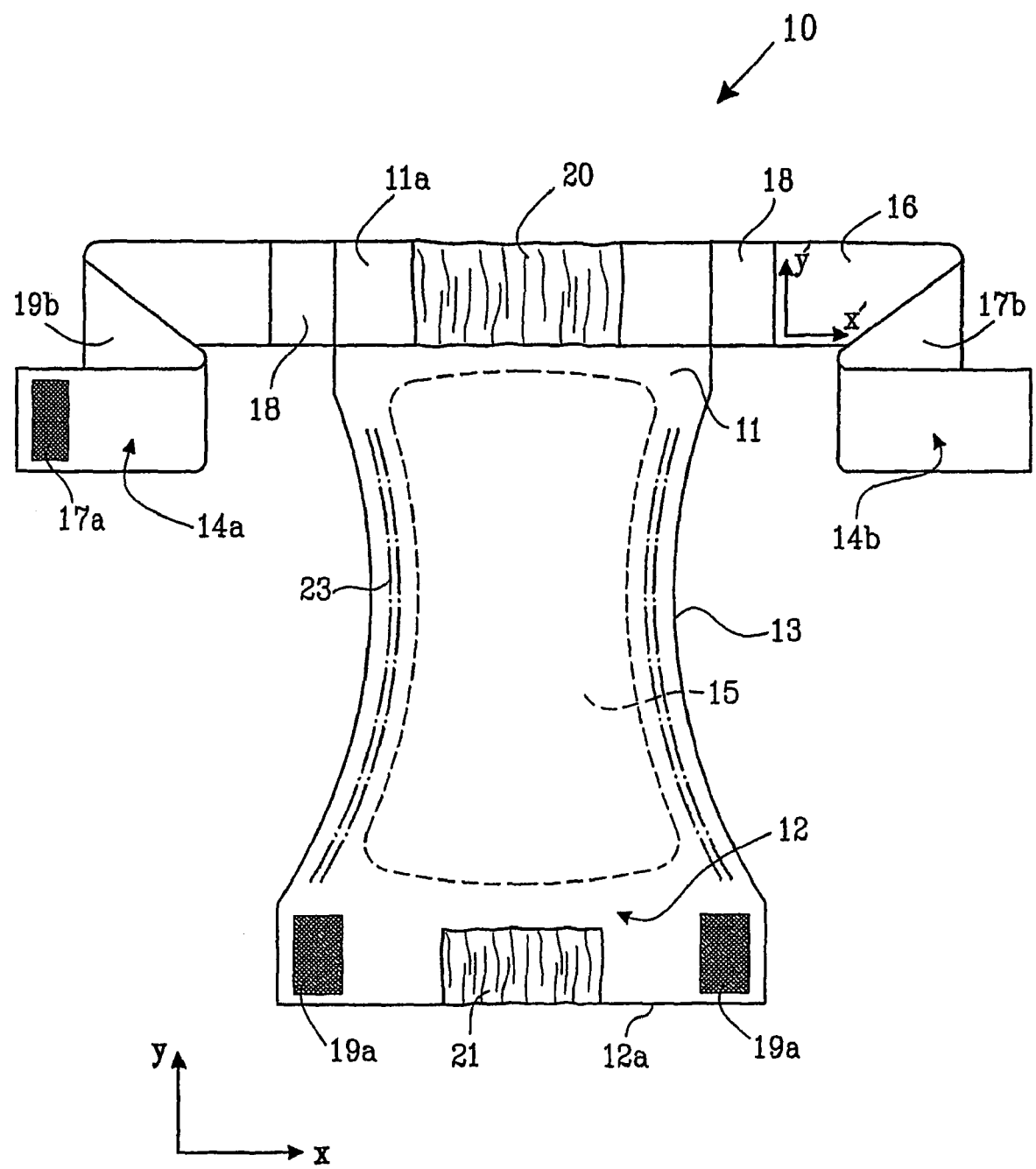
FIG. 1 shows a belted absorbent garment according to an embodiment of the invention.

FIG. 1 shows an embodiment of an absorbent garment in the form of a diaper or incontinence guard 10 comprising a first body panel 11, which in the embodiment shown in the drawings is the part of the garment that, in use, is intended to extend over the back and the rear hip area of the user. The garment also comprises a second body panel 12, which in the shown embodiment is the part of the pant diaper that, in use, is intended to extend over the stomach and front hip area of the user. Each of said first and second body panels 11 and 12 has a waist portion 11a and 12a respectively. It is to be understood that alternatively the first body panel 11 may be the front body panel and the second body panel 12 may be the back body panel. The crotch portion 13 of a garment 10 is the part of the garment that in use is intended to extend through the user's crotch area, between the legs. An absorbent core 15 is disposed in the crotch portion 13 and extends into the front and back body panels 11 and 12. The absorbent garment has a transverse direction x and a longitudinal direction y.

The "absorbent core" is the absorbent structure disposed between the two coversheets (not shown) of the absorbent garment in at least the crotch region thereof. The absorbent core 15 can be of any conventional kind. Examples of commonly occurring absorbent materials are cellulosic fluff pulp, tissue layers, highly absorbent polymers (so called super-absorbents), absorbent foam materials, absorbent non-woven materials or the like. It is common to combine cellulosic fluff pulp with super-absorbent polymers in an absorbent core. Super-absorbent polymers are water-swellable, water-insoluble organic or inorganic materials capable of absorbing at least about 20 times their own weight of an aqueous solution containing 0.9 weight percent of sodium chloride. Organic materials suitable for use as super-absorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred super-absorbent materials are further surface cross-linked so that the outer surface or shell of the super-absorbent particle, fibre, flake, sphere, etc. possesses a higher crosslink density than the inner portion of the super-absorbent.

A high liquid storage capacity is provided by the use of high amounts of super-absorbent material. For an absorbent core comprising a matrix of hydrophilic fibres, such as cellulosic fibres, and super-absorbent material, the proportion of super-absorbent material is preferably between 10 and 90% by weight, more preferably between 30 and 70% by weight.

It is conventional for absorbent garments to have absorbent cores comprising layers of different properties with respect to liquid receiving capacity, liquid distribution capacity and storage capacity. The thin absorbent bodies, which are common in, for example, diapers and incontinence guards, often comprise a compressed, mixed or layered structure of cellulosic fluff pulp and super-absorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

A pair of belt sections 14a, 14b, is attached to the waist portion of the first body panel 11 each comprising an elastic panel 18, such as an elastic laminate, in the exemplified embodiment. The inelastic parts 16 of belt sections 14a and 14b are for example made of a laminate of a carrier material, which forms the external surface of the belt, and a soft non-woven, which forms the inside of the belt which is intended to be in direct contact with the skin of the user. A suitable non-woven material can be a spun-bonded material of polypropylene or polyethylene fibres for example. Conjugate fibres may also be used. Another suitable non-woven material is formed from a carded thermo-bonded material of polypropylene, polyester or conjugate fibres for example. The external surface of the belt sections, for example the carrier material, should be adapted to function as a reception surface for fastening means. In cases where the fastening means is a hook fastener a non-woven material may be used as a carrier material. In cases where the fastening means is a tape tab, a plastic film can also be suitable as reception material as well as non-woven material.

For elastic laminates it is preferred that the first and second layers of fibrous material are chosen so that they, in combination with the intermediate elastic film layer, provide a soft and cloth-like feel to the laminate. Examples of suitable materials are carded webs and spun-bonded materials. Examples of suitable polymers used in the fibrous materials are polyethylene, polyesters, polypropylene and other polyolefin homo-polymers and copolymers. Natural fibres, for example cotton, may also be used as long as they provide the required properties. A mixture of polymers can contribute to a higher flexibility of the non-woven layer.

The elastic film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials.

For reasons of comfort it is advantageous if the total basis weight of the laminate can be kept low. Thus, although a total basis weight of about 150 g/m$^2$ is acceptable, a total basis weight of 130 g/m$^2$ or less is preferred. The basis weight should be at least 25 g/m$^2$.

In practice the length of a belt section 14a, 14b, i.e. the length of a belt section from the longitudinal peripheral edge of the chassis of an absorbent garment to the distal end of the belt section, may, for example, be 290 mm, 340 mm, 400 mm or 510 mm and the length of an elastic panel 18 (as measured in the transverse direction of the belt) may be 72 mm, 85 mm, 100 mm or 127 mm respectively, i.e. up to 25% of the length of the belt section. The total length of the belt is defined as the total combined length of the two belt sections 14a, 14b and the width of the body panel between the longitudinal peripheral edges to which the belt sections 14a, 14b are fastened along the waist portion 11a of the garment. Each belt section 14a, 14b comprises a substantially inelastic part 16 and an elastic panel 18 that is arranged to be capable of being elongated in a substantially transverse direction (x'). The belt sections 14a and 14b are intended to be wrapped around the waist of the user of the absorbent garment and fastened together by means of first fastening means 17, for example a mechanical fastener, especially a hook-and-loop fastening means. Said first fastening means 17 comprises a primary fastener 17a located close to the distal edge of one belt section 14a, such as a hook member, and a secondary fastener 17b on the opposite belt section 14b. The secondary fastener 17b is a reception member for the first fastener 17a. For a hook member the secondary fastener 17b (reception member) is a loop material. Preferably at least a substantial part of the external surface of said opposite belt member 14b acts as a loop material, usually in the form of a fibrous non-woven material.

The external surface of the opposite belt section, especially if it comprises a fibrous non-woven, may function as a loop member. Further examples of mechanical fasteners are button and holes or button loops, snap fasteners and the like. The buttons can either be fastened to the belt or to the garment. The proximal edge of each elastic panel 18 is located within 5 cm, preferably within 3 cm of the peripheral longitudinal edge of the waist portion 11a of the absorbent garment. Any number of elastic panels 18 could however be located anywhere along a belt section 14a, 14b of a belted absorbent garment.

A "hook-and-loop fastener" refers to complementary fastening means having a "hook" portion (primary fastener) and a "loop" portion (secondary fastener) and which are re-fastenable. The term "hook" as used herein refers to any element capable of engaging another element, the so called "loop" portion. The term "hook" is not limited to only "hooks" in its normal sense, but rather encompasses any form of engaging elements, whether uni-directional or bi-directional. The term "loop" is likewise not limited to "loops" in its normal sense, but also encompasses any structure capable of engaging with a "hook" fastener. Examples of "loop" materials are fibrous structures, like non-woven materials. Hook-and-loop fasteners are for example available from Velcro, USA. Alternatively the first fastening means 17 is an adhesive fastening means such as a tape tab (primary fastener 17a), wherein the external surface of opposite belt section 14b may be of a material to which the tape can adhere (secondary fastener 17b). The width of the belt sections 14a and 14b (as measured in the longitudinal direction (y)) should be between 50-160 mm.

A suitable non-woven material can be a spun-bonded material of e.g. polypropylene or polyethylene fibres. Conjugate fibres may also be used. Another suitable non-woven material is formed from a carded thermo-bonded material of e.g. polypropylene, polyester or conjugate fibres.

Second fastening means 19 are further provided to fasten the front panel 12 to the external surface of at least one of the belt sections 14a, 14b. The second fastening means 19 comprises a primary fastener 19a located at the lateral edges of the waist portion 12a of the front panel 12 and a secondary fastener 19b (reception surface) on the external surface of at least one belt section 14a, 14b. In case the primary fastener 19a is a hook fastener, a non-woven material may be used as a reception material. In case the primary fastener 19b of the second fastener is a tape tab, a plastic film as well as non-woven material can also be suitable as reception material (secondary fastener 19b).

The front panel 12 is passed between the legs of the user and fastened to the outside of the belt sections 14a, 14b by means of the primary fastener 19a of the second fastening means 19 provided at the lateral edges of the waist portion 12a of the front panel 12. These second fastening means 19 are mechanical fasteners, such as hook and loop fasteners, button and holes or button loops or adhesive tape fasteners.

An elastic member 20 extends in the transverse direction, x', along at least part of the waist portion 11a of the first body panel 11. Said elastic member 20 may be in the form of an elastic web material such as an elastic film, an elastic non-woven, an elastic laminate or the like. The elastic laminate may be a laminate between two or more non-woven layers, two or more film layers or a combination of film and non-woven layers. According to another embodiment of the invention said elastic member 20 may extend continuously along the whole transverse side of the waist portion 11a of the first body panel. The elastic member 20 should have an elasticity of at least 30% as measured in the elasticity test as described herein.

A waist elastic member 21 extends in transverse direction, x, along at least part of the waist portion 12a of the second body panel 12. The waist elastic member 21 may be an elastic web material such as an elastic laminate, an elastic film, an elastic non-woven or the like contractably attached between the inner and outer coversheets, to the external side of the outer coversheet or to the user-facing side of the inner coversheet. Alternatively it comprises two or more elastic threads or strips contractably affixed between the outer and inner coversheets.

The leg openings may be elasticized, said elastification is usually accomplished by a plurality of elastic members 23, such as elastic threads that are contractably affixed between the outer and inner coversheets. The garment may also be provided with so called barrier cuffs, in order to provide an improved security against leakage. These barrier cuffs may in some instances replace leg elastics.

Figure 2:
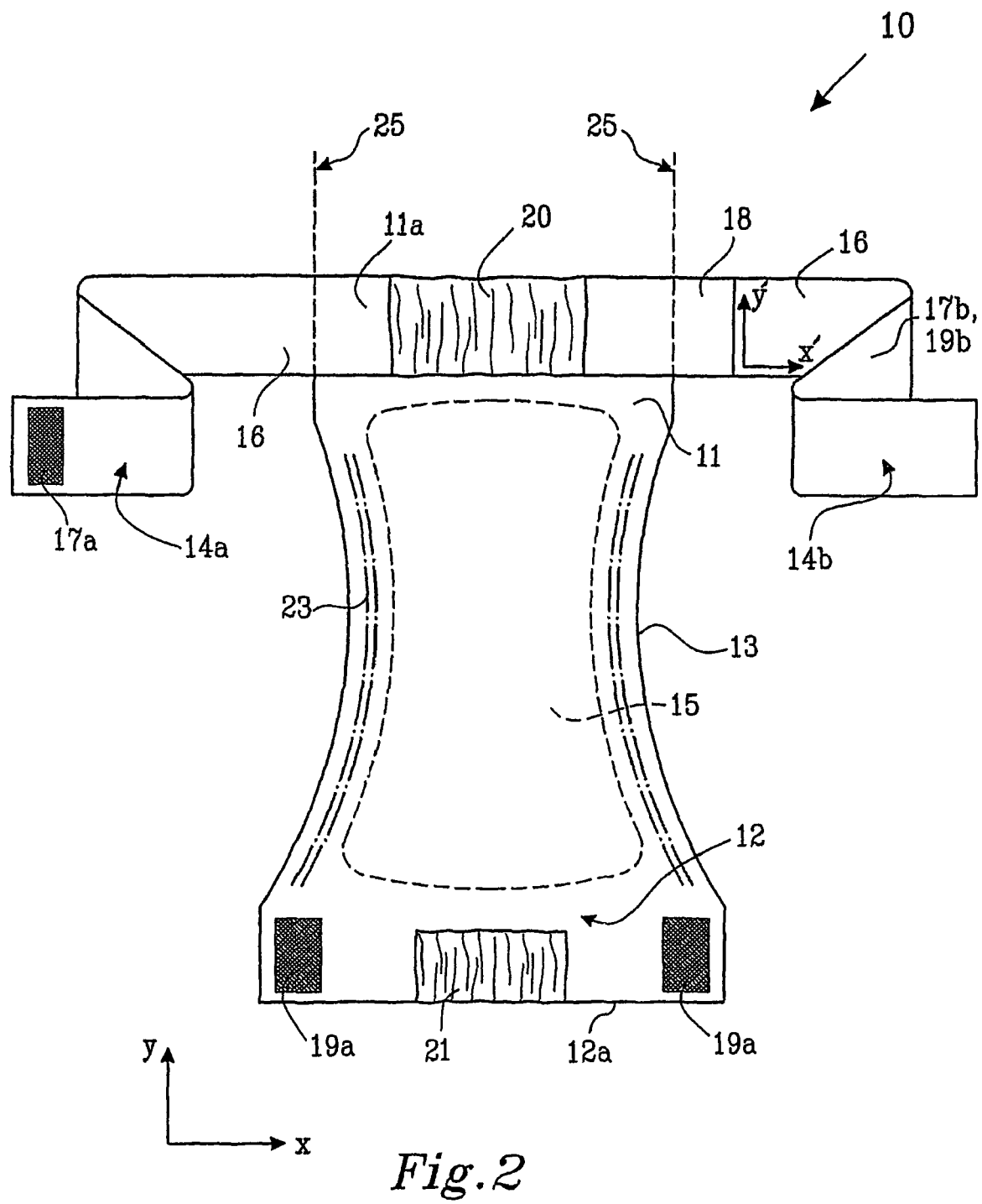
FIG. 2 shows a belted absorbent garment according to another embodiment of the invention.

FIG. 2 shows another embodiment of an inventive absorbent garment 10. The absorbent garment 10 shown in FIG. 2 differs from that shown in FIG. 1 in that instead of attaching two opposing belt sections to the longitudinal (y) peripheral edges of the waist portion 11a of the back body panel 11, a belt is attached to the transverse (x) peripheral edge of the waist portion 11a whereby a "belt section" is defined as that part of the belt transversely outside of lines 25 in a direction away from the chassis of the absorbent garment 10. The total length of the belt is defined as the length from the distal end of one belt section 14a to the distal end of the other belt section 14b.

Figure 3:
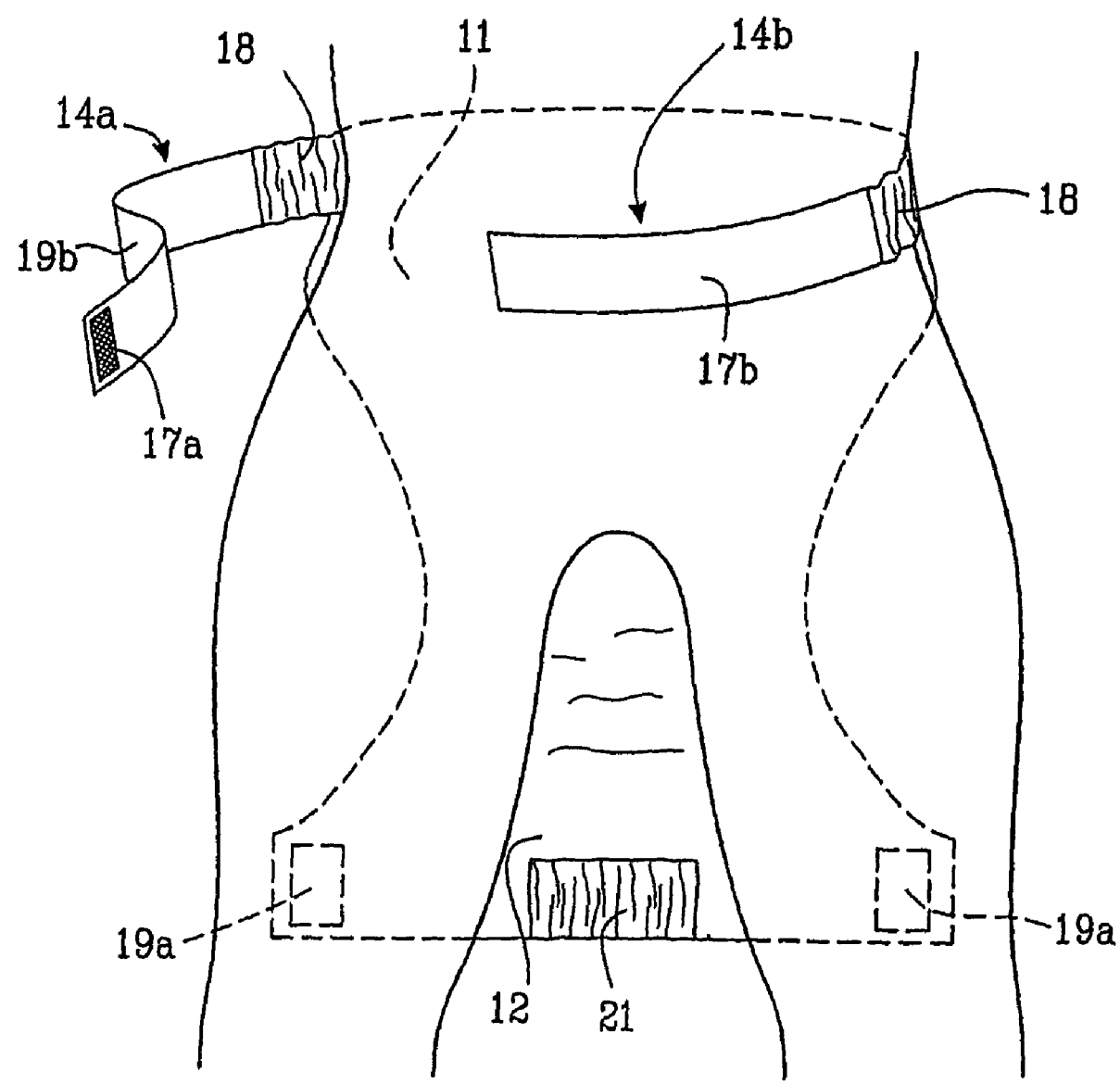
FIGS. 3 & 4 illustrate how a belted absorbent garment is put on a user.
Figure 4:
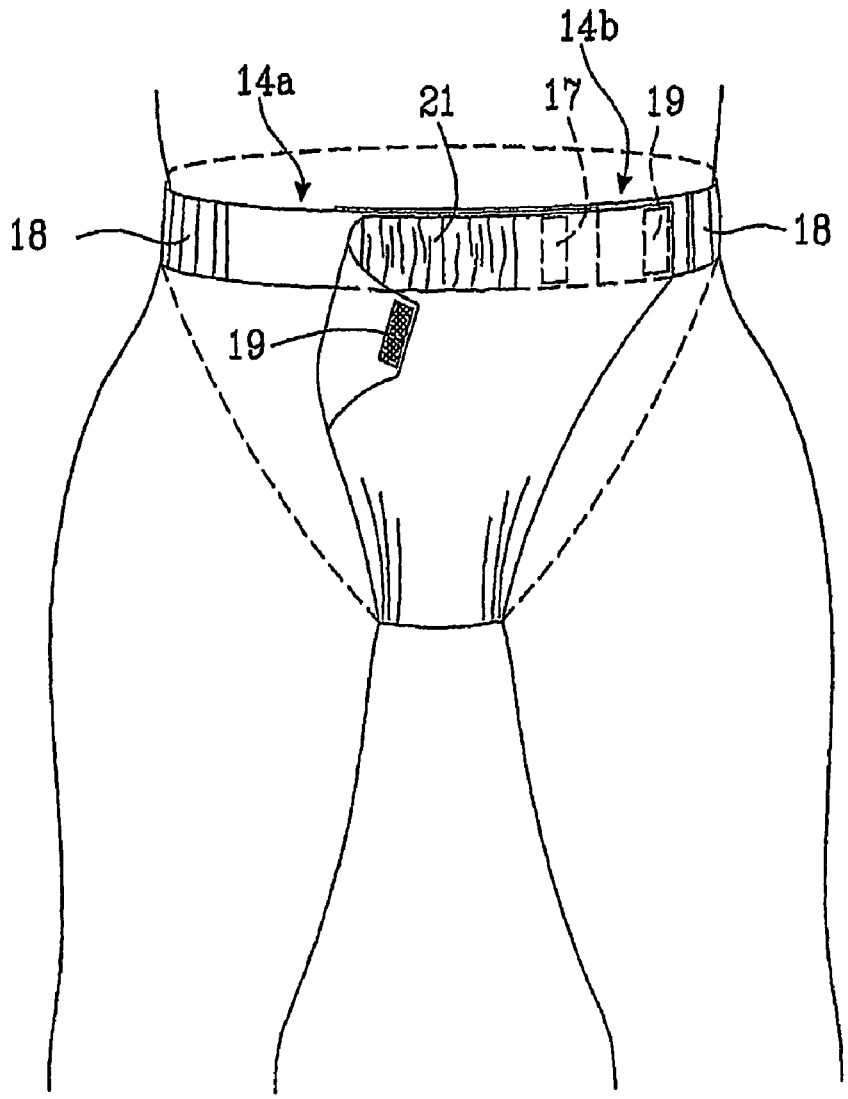

FIGS. 3 and 4 show how two belt members 14a, 14b are intended to be wrapped around the waist of a user and fastened together by fastening means. Belt sections 14a, 14b attached to the waist portion of the back body panel 11 are wrapped around the waist of the user and fastened together by means of the first fastening means 17. The second fastening means 19 on the front body panel 12 are then fastened to the external surface of at least one of the belt sections (14a, 14b) so that the absorbent garment assumes a pant-like shape.

Figure 5:
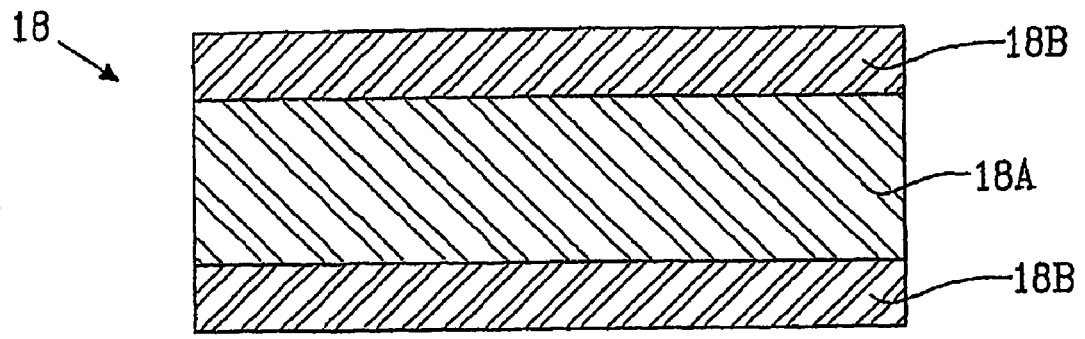
FIG. 5 shows a cross section of an elastic panel according to an embodiment of the invention, FIGS. 6-9 schematically show the Cyclic Waist Expansion Test Apparatus according to an embodiment of the invention.

FIG. 5 shows schematically an elastic laminate that is suitable for use as an elastic panel 18. The elastic laminate comprises an elastic film 18A comprising a styrene butadiene copolymer, sandwiched between two necked non-woven layers 18B, such as polypropylene or polyethylene non-woven layers, whereby the layers of said elastic laminate are ultrasonically bonded together. According to an embodiment of the invention at least one belt section of a belted absorbent garment comprises at least one such elastic laminate. When said at least one belt section is attached to a longitudinal peripheral edge of a body panel 12 of an absorbent garment 10, a proximal edge of the elastic panel 18 is preferably located within 5 cm, more preferably within 3 cm of the longitudinal peripheral edge of the body panel 12 or in any other position along the belt section. In the case where a belt section comprises two or more elastic panels 18 the additional elastic panels may be located in any positions along the belt section.

Figure 6:
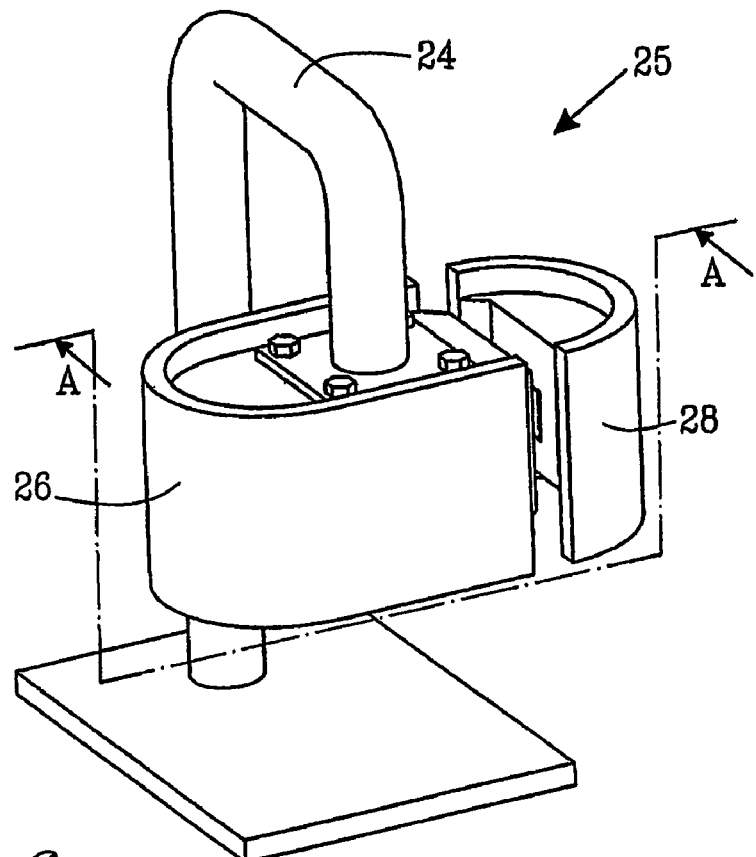

FIG. 6 schematically shows a perspective view of the Cyclic Waist Expansion Test Apparatus 25 according to an embodiment of the invention. The test equipment 25 comprises a stand 24 that supports two contoured plates 26, 28 which are formed to mechanically simulate a human user's waist. The contoured plates 26, 28 are supported by the stand 24 in such a way that the stand 24 does not hinder any part of an absorbent garment from being wrapped around the contoured plates 26, 28. The belt sections 14a, 14b are wrapped around the contoured plates 26, 28 and fastened together in a stretched position, as will be described below. The second body panel 12 is then fastened to the external surface of at least one of the belt sections 14a, 14b in the manner described above. One must make sure that the body panels 11,12 lie flat against the contoured plates 26,28 when putting the absorbent garment onto the Cyclic Waist Expansion Test Apparatus 25.

Figure 7:
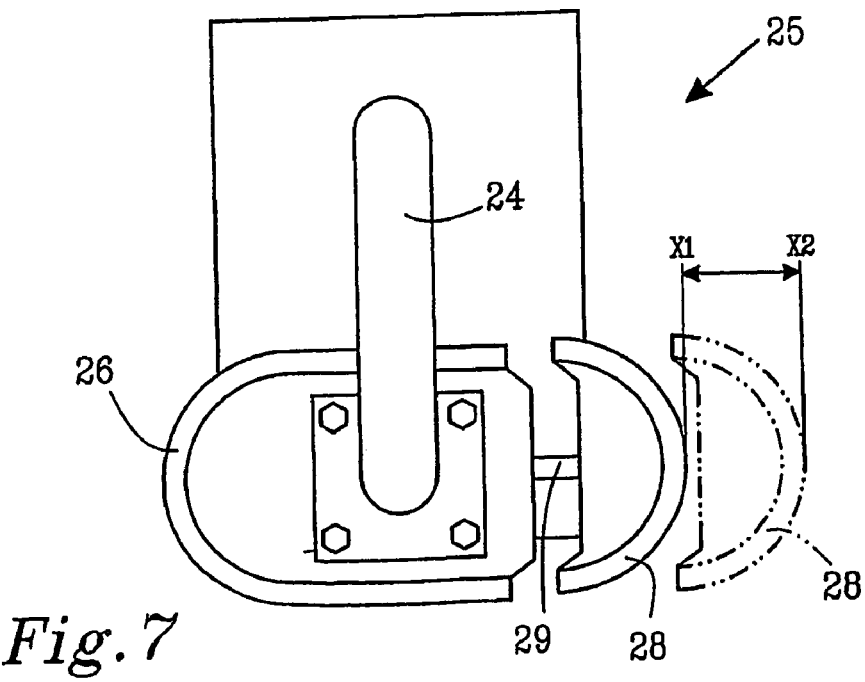

FIG. 7 shows the Cyclic Waist Expansion Test Apparatus 25 from above. Once a belted absorbent garment has been fastened around the contoured plates 26, 28, actuating means 27, 29 force the second contoured plate 28 away from the first mechanical member 26 from its initial position X1 to an outer position X2 and then back to its initial position X1 (which constitutes one expansion/contraction cycle) a number of times so as to simulate the expansion and contraction of a user's waist as he/she moves. The apparatus' mechanical motion speed (V) is set to 25 cycles per minute. The second mechanical member 28 is arranged to move through a distance of up to 100 mm or more from the first mechanical member 26.

Figure 8:
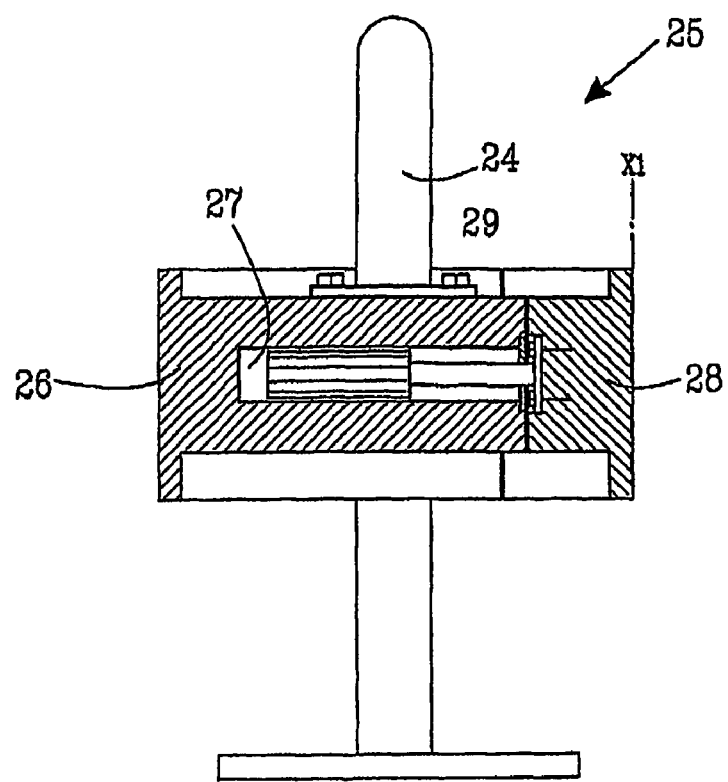
Figure 9:
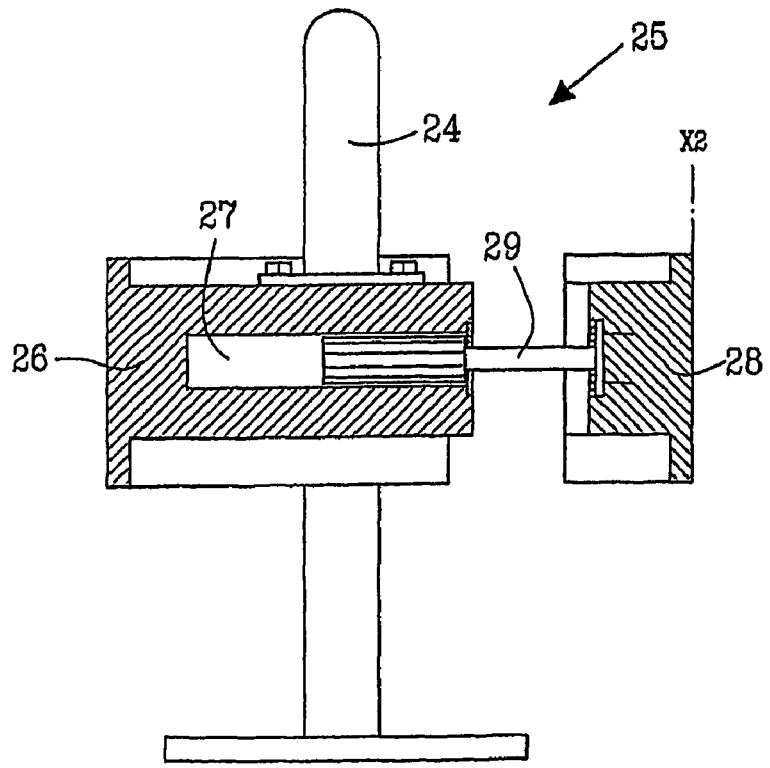

FIGS. 8 and 9 show cross-sections of the Cyclic Waist Expansion Test Apparatus 25 (as viewed in the vertical plane A-A shown in FIG. 6). The contoured plates 26, 28 are shown in their initial position X1 and when the contoured plates 26, 28 are positioned apart at position X2 respectively. The first fixed contoured plate 26, which incorporates a cylinder 27, is mounted directly on the stand 24. The second movable contoured plate 28 incorporates a piston 29 that is moved into and out of the cylinder 27 and is free to move with respect to the first fixed contoured plate 26. The actuating means 27, 29 may comprise a pneumatic or hydraulic cylinder or piston, as in the illustrated embodiment, or any other means for moving the two contoured plates 26, 28 together and apart. One or more support rods for supporting the second contoured plate 28 may be provided between the contoured plates 26, 28 to support the second contoured plate 28 as it moves.

Figure 10:
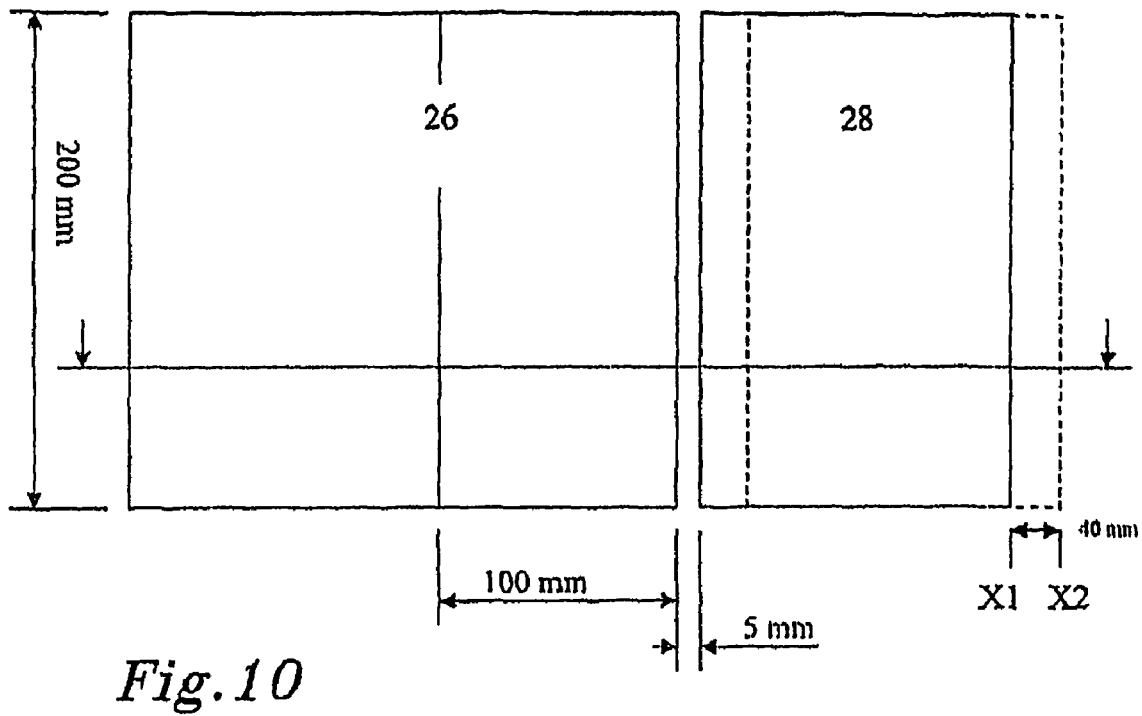
FIGS. 10-22 illustrate the steps of the Cyclic Waist Expansion Test for determining how well a belted absorbent garment will stay in place on a user's waist when in use.
Figure 11:
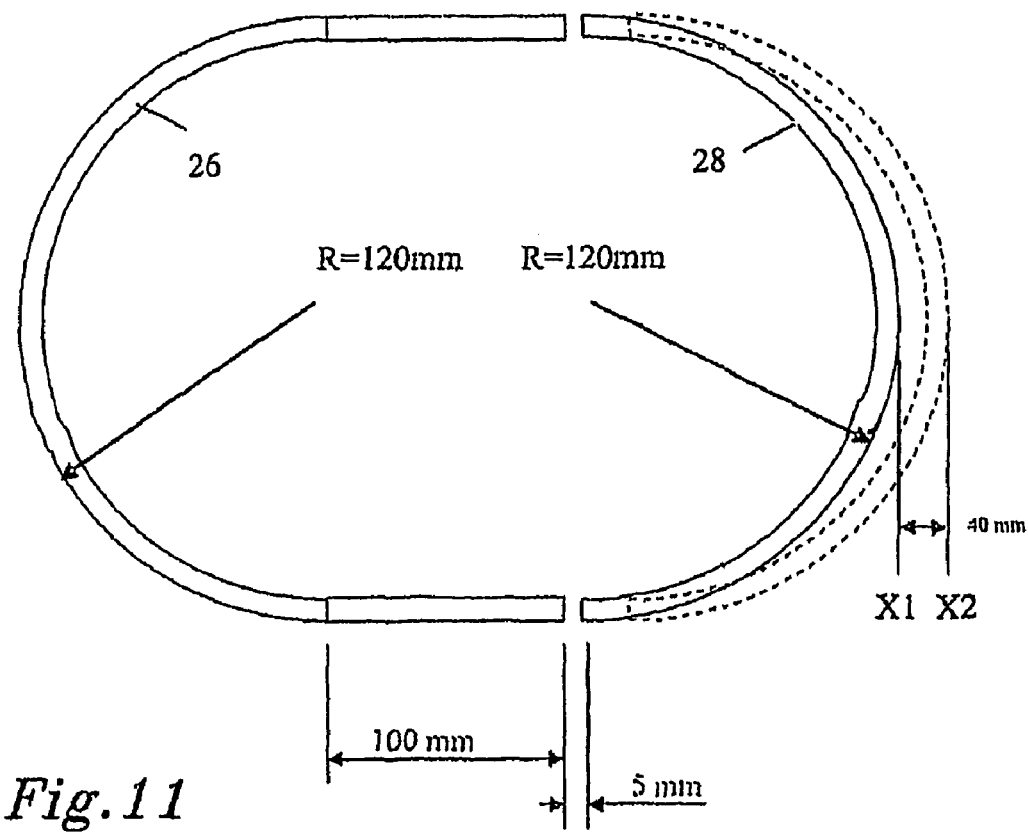
Figure 12:
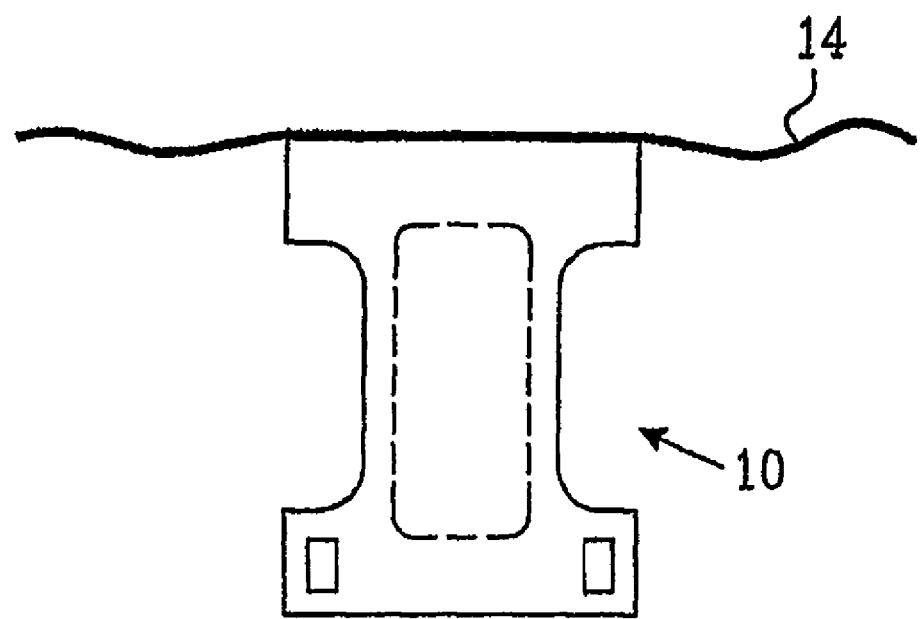

FIGS. 10 and 11 schematically show the two contoured plates 26, 28, of the Cyclic Waist Expansion Test Apparatus 25 from the side and from above respectively. The first contoured plate 26 has a substantially U-shaped cross-section and is constituted of a half circle of outer radius 120 mm and two straight parallel portions, 100 mm in length, extending from each end of the half circle in the transverse direction x. The second contoured plate has a substantially C-shaped cross-section and is constituted of a half circle of outer radius 120 mm. The two contoured plates are assembled with the open ends of their respective U- and C-shaped cross sections facing one another so as to form a substantially elliptical shape resembling the shape of a human waist. The second contoured plate 28 is moved through a predetermined distance from an inner position X1 to an outer position X2 mechanically. This predetermined distance is 40 mm when carrying out the Cyclic Waist Expansion Test, giving a circumference change of 80 mm. Both contoured plates 26,28 have a height of 200 mm and their surface comprises austenitic stainless steel (DIN 1.4301, SIS 2333, AISI 304) having a grain size of 0.3 µm. The surface finish is of the mechanical members 26, 28 is produced by applying Scotch Brite™ to the surface of the metal to give a fine scratch pattern appearance. It is also useful in reducing tool wear, i.e. removal of abrasive surface oxides.

When the contoured plates 26, 28 are in their inner position X1 there is a distance of 5 mm between them. Such a distance is necessary to ensure that absorbent garments are not clamped between the contoured plates. If the shortest distance between the two contoured plates were 0 mm, there would be a risk of the absorbent garments getting stuck in the nip between the two contoured plates instead of falling therefrom once their belts had been permanently deformed.

The test equipment 25 has a circumference of 96.4 cm and is arranged to accommodate absorbent garments that have a total belt length from 100 cm, whereby there is an overlap of 4 cm between belt sections. There is actually no upper limit of the total belt length of absorbent garments that can be tested on the test equipment since the upper limit is determined by how the absorbent garment is fastened around the waist of a user. However, if one belt section is arranged to be fastened to the other belt section, the total belt length is preferably not greater than 135 cm. Ten Newtons is considered to be a suitable force when applying the product on a user.

With reference to FIGS. 12-22, the Cyclic Waist Expansion Test comprises the steps of:

Ensuring that the second contoured plate 28 is set at its inner position X1.

Unfolding the absorbent garment 10 and positioning the edge of a first belt section 14b that comprises the secondary fastener 17b of the first fastening means, parallel to the upper edge of a straight portion of the first contoured plate 26.

Figure 13:
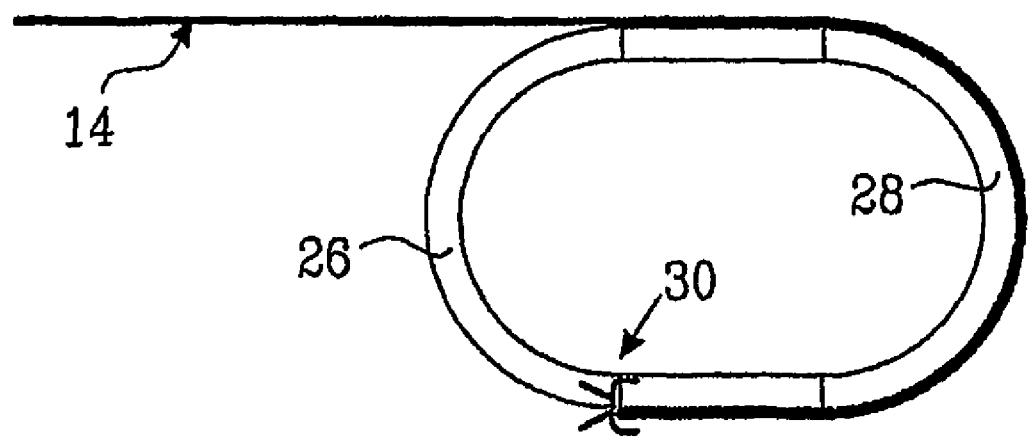
Figure 14:
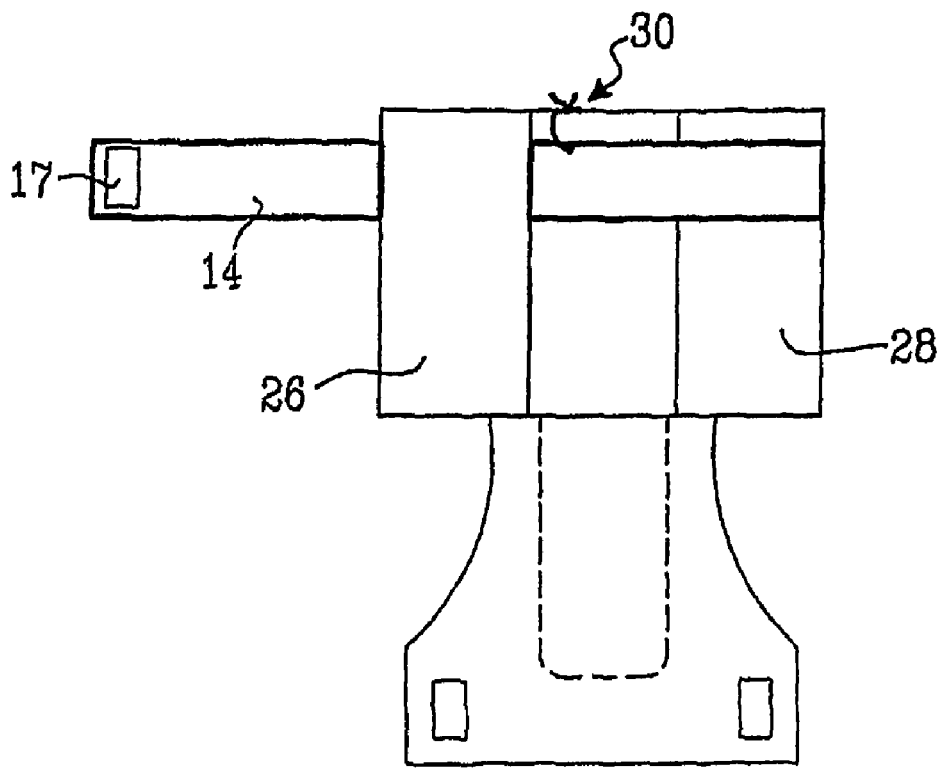

Securing said first belt section 14b to the first contoured plate 26 by clamping means, such as a clip 30 (see FIGS. 13 and 14).

Wrapping the absorbent garment peripherally around the contoured plates 26, 28 ensuring that the uppermost edge of the belt section 14b does not wrap around the upper edge of the contoured plates 26, 28 and that the front and back waist portions 11a, 12a of the absorbent garment are centered on respective straight portions of the first contoured plate 26. The elastic panels 18 of the belt sections should then be located on the rounded portions of the first and second contoured plates 26, 28.

Figure 15:
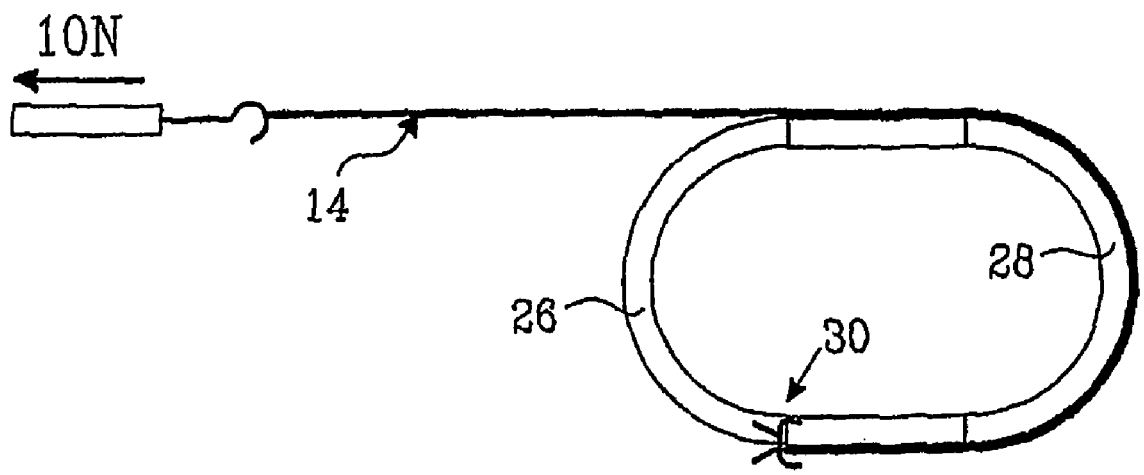
Figure 16:
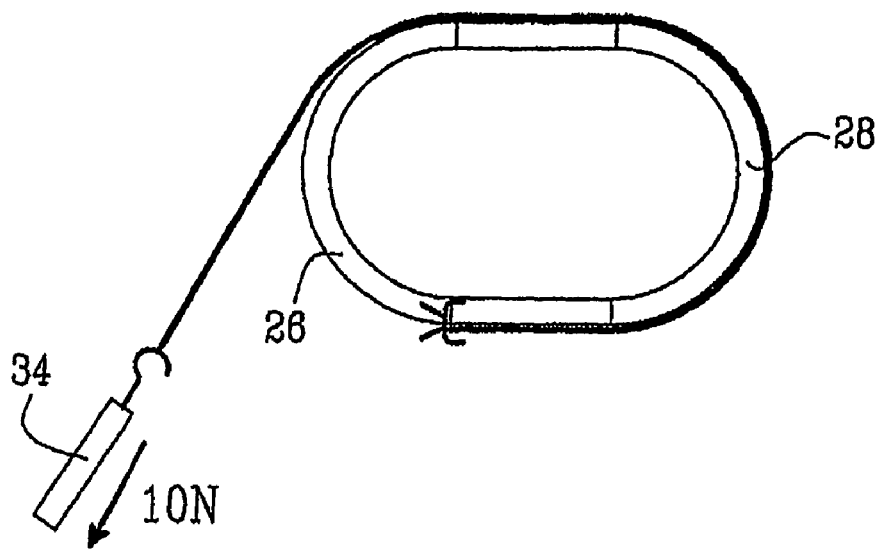
Figure 17:
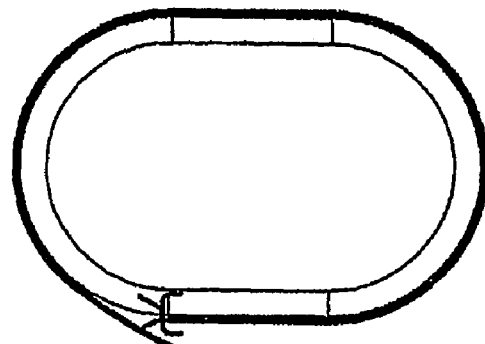
Figure 18:
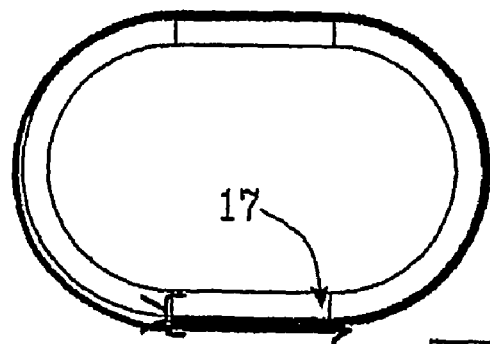

Using a dynamometer 34 to stretch the free, i.e. non-clamped, second belt section 14a that comprises the primary fastener 17a of the first fastening means 17 to a force of 10 N (see FIG. 15). Said free second belt section 14a is stretched in a direction that is collinear to the plane of the outer surface of the straight portion of the first contoured plate 26 which is closest to the free second belt section 14a. FIG. 15 illustrates the direction in which said free second belt section 14a is initially stretched. Once the free second belt section 14a has been stretched to a force of 10 N, the dynamometer 34 is moved around the contoured plates 26, 28 making sure that a force of 10 N is maintained during the whole process (see FIGS. 16-18), thus ensuring that all absorbent garments are fastened with the same force around the Cyclic Waist Expansion Test apparatus and that the elastic panels of the absorbent garments are all stretched by the same amount.

Securing the free second belt section 14a to the clamped first belt section 14b by pressing the primary fastener 17a of the first fastening means 17 onto the outer surface of the clamped first belt section 14b with a thumb for example while the tensioning force is maintained, whereby the fastening means are attached directly to the outer surface of the belt section 14b or a reception part located on the outer surface of the belt section 14b acting as a secondary fastener 17b. The dynamometer is then removed.

Figure 19:
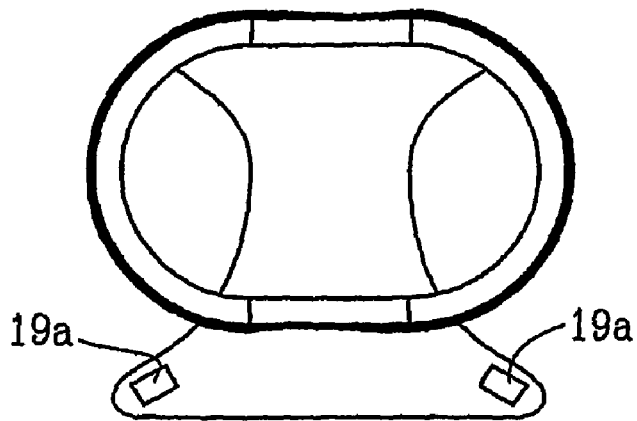
Figure 20:
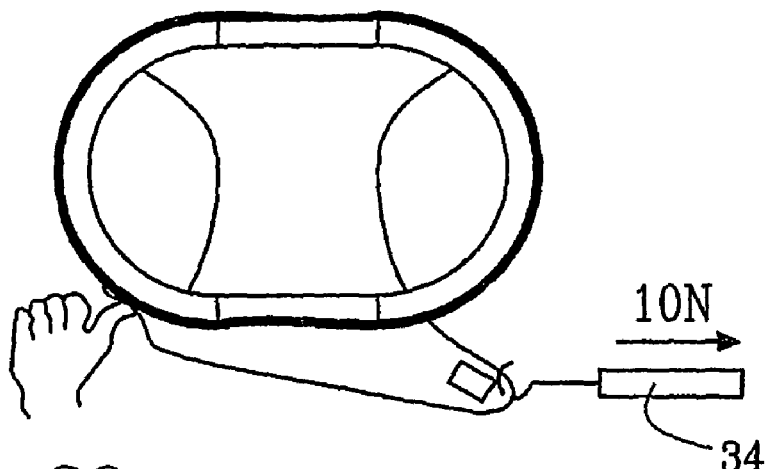
Figure 21:
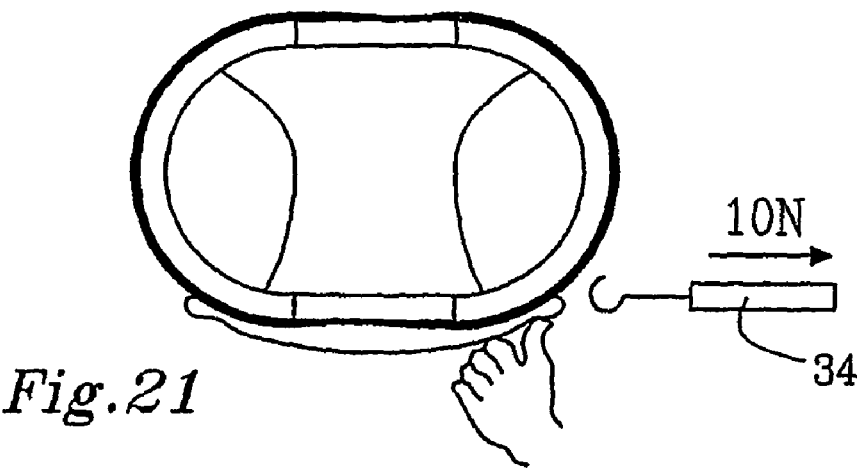

Wrapping the hanging crotch portion 13 of the absorbent garment under the contoured plates 26, 28 and securing second fastening means 19, that are located on a body panel of the absorbent garment, to the belt sections 14a, 14b that are fastened around the contoured plates 26, 28. The second fastening means 19 may comprise two individual primary fasteners 19a located on opposite sides of the body panel (as shown in FIG. 19), whereby a first primary fastener 19a is pressed onto the belt sections 14a, 14b while a dynamometer 34 is stretching the opposite side of the body panel to a force of 10N in a direction parallel to the straight portion of the first contoured plate 26. The dynamometer 34 is removed while pressing the second primary fastener 19a to the belt sections 14a, 14b. The dynamometer 34 therefore stretches the elastic material in the waist area of the body panel of the absorbent garment 10 and the second fastening means 19. Alternatively said second fastening means 19 comprises a single fastener, in which case said single fastener is attached to the belt sections 14a, 14b while a force of 10 N is used to keep apart the edges of the body panel 12.

Removing the dynamometer.

Figure 22:
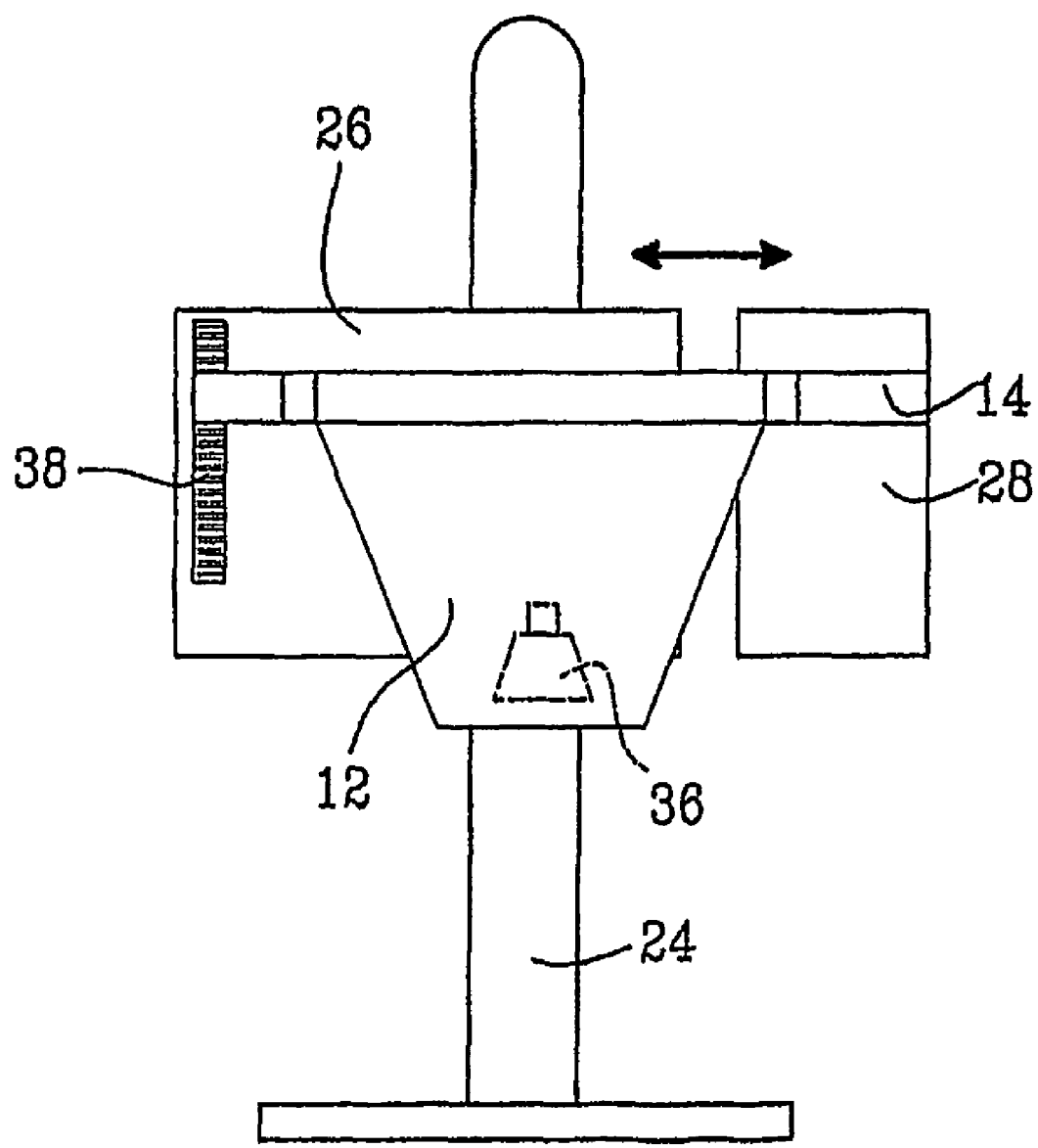

Putting a weight 36 of 300 grams inside the crotch portion of the absorbent garment (see FIG. 22).

Marking or noting the position of the top edge of the belt on the Cyclic Waist Expansion Test Apparatus.

Starting the pneumatic cylinder and letting the two contoured plates 26, 28 move through ten expansion and contraction cycles. When the last cycle is complete the two contoured plates 26, 28 are arranged to stop at the inner position X1 at a distance 5 mm apart.

Marking or noting the position of the top edge of the belt thirty seconds after the tenth expansion and contraction cycle had been completed and measuring/calculating the vertical distance between the first and second marks or positions, thus providing the distance through which absorbent garment has slipped if the absorbent garment still remains on the Cyclic Waist Expansion Test.

In order to pass the Cyclic Waist Expansion Test the absorbent garment 10 must not slip down more than 15 cm from its initial position on the Cyclic Waist Expansion Test during ten expansion/contraction cycles and during at least 30 seconds after completion thereof. Such a belted absorbent garment or its packaging may then be marked with information and/or a parameter that is indicative of how well said belted absorbent garment stays in place on a user's waist when in use.

FIG. 22 shows a belted absorbent garment 10 fastened around the test equipment. According to an embodiment of the invention the test equipment comprises a vertical scale 38 so that the initial position of an edge of the belt 14 of the belted absorbent garment 10 may be recorded as well as its position after each, or all of the expansion and contraction cycles. The actuating means may then move the contoured plates 26, 28 through ten expansion and contraction cycles for example (where one such cycle involves moving the movable contoured plate 28 from X1 to X2 and back to X1 again).

Ten samples of each of five different commercially available belted absorbent garments were tested under the same conditions using the Cyclic Waist Expansion Test. Ten samples of the absorbent garment according to the present invention were also tested and compared to the commercially available products. The inventive absorbent garment was a TENA Flex product comprising elastic panels in its belt sections as shown in FIG. 1. The elastic panels comprised Fabriflex™ 306 from Tredegar. The length of each belt section was 355 mm. The length of attached elastic material in the transverse direction of the belt was 50 mm, whereby the active elastic length of the attached elastic material was 30 mm. The proximal edge of each elastic panel was located 2 mm from the peripheral longitudinal edge of the body panel to which the belt section comprising said elastic panel was attached.

Fabriflex™ 306 is an elastic laminate material made of a soft PP/PE nonwoven of 25 g/m² outer layers coextruded with a 57 g/m² elastic film inner layer. The laminate material has the following parameters.

| | |
|---|---|
| basis weight | 120 g/m² ± 20 |
| bond strength | 6.0 N/25.4 mm −5.0/+13.0 |
| CD Tensile at 25% elongation | 1.9 N/25.4 mm ± 0.7 |
| CD Tensile at 50% elongation | 3.0 N/25.4 mm ± 3.0 |
| CD Tensile at Nonwoven break | 23.8 N/25.4 mm 15.4 |
| CD elongation at Nonwoven break | 209% |
| CD Unload at 25% | 0.63 N/23.4 mm ± 0.15 |
| CD Unload at 50% | 2.2 N/25.4 mm ± 1.2 |

All of the dimensions of elastic panels along the length of a belt in the transverse direction of the absorbent garment which are given in this document refer to the active elastic length i.e. the length of the elastic material of the belt, which can be elongated on application of an elongating force in the transverse direction of the absorbent garment and retracted when releasing the force, whereby "elastic material" is as defined according to the aforementioned elasticity test.

The elastic laminate was elongated by about 12 mm on application of a force of 10 N (material sample 100 mm wide and distance between clips 30 mm). It took a force of 14 N to elongate it by 60% and a force of 38 N to elongate it by 120%. According to a preferred embodiment of the invention the maximum force required to elongate a suitable elastic material by 60% should not be more than 15 N. The inelastic part of the belt must be made of material that does not stretch or elongate too much when it is subjected to a force of up to 30 N/100 mm. A suitable material was found to be a three layer non-woven laminate such as Lamitex™ 92 from Tenotex.

Lamitex™ 92 is a laminate comprising a loop layer of Tric Trac 30 g/m², hydrophilic, carded, 2.2 dtex, white, 100% PP; a support layer of Spunten 40 g/m² Phop, hydrophobic, spunbond, 2.2-2.5 dtex, white, 100% PP; and a skin layer of Spunten 22 g/m², hydrophobic, spunbond, 2.2-2.5 dtex, white, 100% PP.

The following table shows the number of cycles for which each product remained within 15 cm of its initial position on the Cyclic Waist Expansion Test apparatus.

The symbol "√" indicates that the product passed the test, i.e. it remained fastened within 15 cm from its initial position on the Cyclic Waist Expansion Test apparatus during ten expansion/contraction cycles and for at least 30 seconds after the completion of ten expansion and contraction cycles.

The symbol "X" indicates that the product failed the test, i.e. that it slipped 15 cm or more from its initial position on the Cyclic Waist Expansion Test apparatus during ten expansion and contraction cycles or within 30 seconds after the completion of ten expansion and contraction cycles.

Waist Expansion Test Apparatus ensuring that the top edge of the belt of each garment was secured in a position parallel to the top edge of the mechanical members. The table below shows the distance through which five inventive belted absorbent garments slipped during the Cyclic Waist Expansion Test.

| Inventive garment | Slip distance |
|---|---|
| A | 5.4 cm |
| B | 4.5 cm |
| C | 4.6 cm |
| D | 4.4 cm |
| E | 4.6 cm |

Further modifications of the invention within the scope of the claims would be apparent to a skilled person. If the test apparatus is to be used as a general method of testing an absorbent garment the test apparatus may be modified. The mechanical members of the apparatus may for example be of any shape and size, such as in the form of metal rods. An

| | Supplier: | | | | | |
|---|---|---|---|---|---|---|
| | Ontex, | First Quality, | Hartman, | Abena | SCA, | SCA, |
| | | | Product: | | | |
| | Euron Wings Medium Extra | Prevail Fits to a T Medium | MoliFlex Premium Medium | Abri-Wing Medium | TENA Flex Plus Medium | Inventive garment |
| | | | Product code: | | | |
| | PL7: 1230054905 | — | 504717081 | — | GP41320540 | — |
| | | | Bag code: | | | |
| | — | 5 18 05:08 11/05 | — | 0524 1252 05, 08, 24 | — | — |
| Sample 1 | 7 cycles X | 10 cycle X | 3 cycles X | 2 cycles X | 9 cycles X | 10 cycles √ |
| Sample 2 | 7 cycles X | 10 cycles X | 4 cycles X | 1 cycle X | 10 cycles X | 10 cycles √ |
| Sample 3 | 6 cycles X | 10 cycles X | 3 cycles X | 1 cycle X | 10 cycles X | 10 cycles √ |
| Sample 4 | 7 cycles X | 10 cycles X | 4 cycles X | 1 cycle X | 10 cycles X | 10 cycles √ |
| Sample 5 | 9 cycles X | 10 cycles X | 3 cycles X | 1 cycle X | 10 cycles X | 10 cycles √ |
| Sample 6 | 6 cycles X | 10 cycles X | 3 cycles X | 2 cycles X | 10 cycles X | 10 cycles √ |
| Sample 7 | 8 cycles X | 10 cycles X | 4 cycles X | 1 cycle X | 10 cycles X | 10 cycles √ |
| Sample 8 | 7 cycles X | 10 cycles X | 4 cycles X | 1 cycle X | 10 cycles X | 10 cycles √ |
| Sample 9 | 6 cycles X | 9 cycles X | 4 cycles X | 1 cycle X | 8 cycles X | 10 cycles √ |
| Sample 10 | 7 cycles X | 10 cycles X | 3 cycles X | 1 cycle X | 10 cycles X | 10 cycles √ |

The inventive belted absorbent garment was the only product that did not slip down more than 15 cm on the Cyclic Waist Expansion Test Apparatus for at least 30 seconds after the completion of ten expansion and contraction cycles. The inventive belted absorbent garment stayed in place since no permanent deformation of its belt occurred during testing and the belt therefore maintained its initial optimal circumference. All of the other belted absorbent garments slipped and fell off the Cyclic Waist Expansion Test Apparatus after one to ten expansion and contraction cycles.

A test was carried on five inventive belted absorbent garments whereby said garments were fastened to the Cyclic inventive absorbent garment must however be tested on the Cyclic Waist Expansion Test apparatus described in this document.

What is claimed is:

1. An absorbent garment having a longitudinal and a transverse direction and comprising:
    a first body panel, a second body panel and a crotch portion therebetween in the longitudinal direction, each of said first and second body panels having a waist portion, said absorbent garment further being provided with belt sections attached to the waist portion of the first body panel and being adapted to be wrapped around the waist of a user of the absorbent garment and fastened together by a first fastener, the second body panel at its waist portion being provided with a second fastener adapted to be fastened to at least one of the belt sections in such a way that the absorbent garment will assume a pant-like shape, wherein the at least one belt section comprises inelastic panels and at least one elastic panel that extends up to 25% of the length of the belt section in the transverse direction thereof, as measured in the initial non-elongated state of the belt section, and wherein when the absorbent garment is tested on a test apparatus by: (a) fastening a belted absorbent garment around movable mechanical members which are adapted to mechanically simulate a user's waist or hips; and (b) moving said members away from each other using actuating members and moving them back to their initial position so as to simulate the expansion and contraction of a user's waist as he/she moves; the garment does not slip down more than 15 cm from its initial position on the test apparatus during at least ten expansion/contraction cycles of the test apparatus and for at least 30 seconds after being subjected to at least ten expansion/contraction cycles of the test apparatus.

2. The absorbent garment according to claim 1, wherein said at least one elastic panel comprises an elastic film, an elastic non-woven, an elastic laminate such as a stretch activated laminate, a stretch-bonded laminate, a neck bonded laminate, elastic threads that are contractably affixed between web materials or a laminate in which inelastic non-woven layers are laminated to an elastic film layer and the laminate is stretched above the point of failure of the non-woven materials, so that the inelastic layers break.

3. The absorbent garment according to claim 1, wherein said at least one elastic panel comprises an elastic laminate, comprising at least one elastic film layer and at least one non-woven layer, in which the layers have been ultrasonically bonded, adhesively bonded or extrusion bonded, or bonded using a combination of said bonding methods.

4. The absorbent garment according to claim 1, wherein the absorbent garment does not slip down more than 10 cm from its initial position on the test apparatus during at least ten expansion/contraction cycles of the test apparatus and for at least 30 seconds after being subjected to at least ten expansion/contraction cycles of the test apparatus.

5. The absorbent garment according to claim 1, wherein the belt comprises opposed, laterally extending belt sections that are connected to opposite sides of a body panel and at least one belt section comprises at least one elastic panel, the proximal edge of which is located within 5 cm of the peripheral longitudinal edge of the body panel to which said at least one belt section comprising said at least one elastic panel is attached.

6. The absorbent garment according to claim 1, wherein, each elastic panel extends 1-15 cm along the length of a belt section in the transverse direction thereof as measured in the initial non-elongated state of the belt section.

7. The absorbent garment according to claim 1, wherein the length of each belt section in the transverse direction thereof is from 25 to 55 cm as measured in the initial non-elongated state of the belt section.

8. The absorbent garment according to claim 1, wherein the width of the belt in the longitudinal direction thereof is from 50 to 160 mm.

9. The absorbent garment according to claim 1, wherein said belt sections have a transverse and a longitudinal direction and at least one belt section comprises at least one elastic panel that extends up to 15% of the length of the belt section in the transverse direction thereof, as measured in the initial non-elongated state of the belt section.

10. The absorbent garment according to claim 1, wherein said belt sections have a transverse and a longitudinal direction and at least one belt section comprises at least one elastic panel that extends up to 10% of the length of the belt section in the transverse direction thereof, as measured in the initial non-elongated state of the belt section.

11. The absorbent garment according to claim 1, wherein the absorbent garment does not slip down more than 7 cm from its initial position on the test apparatus during at least ten expansion/contraction cycles of the test apparatus and for at least 30 seconds after being subjected to at least ten expansion/contraction cycles of the test apparatus.

12. The absorbent garment according to claim 1, wherein the belt comprises opposed, laterally extending belt sections that are connected to opposite sides of a body panel and the at least one elastic panel has a the proximal edge located within 3 cm of the peripheral longitudinal edge of the body panel to which said at least one belt section comprising said at least one elastic panel is attached.

13. A method for determining how well a belted absorbent garment will stay in place on a user's waist when in use, the method comprising fastening a belted absorbent garment around movable mechanical members which are adapted to mechanically simulate a user's waist or hips; and moving said members away from each other using actuating members, and moving them back to their initial position so as to simulate the expansion and contraction of a user's waist as he/she moves.

14. The method according to claim 13, wherein the method comprises the step of repeating said expansion and contraction cycle by moving the movable members away from each other and back to their initial position a plurality of times.

15. The method according to claim 13, wherein the method comprises adding weight to the belted absorbent garment.

16. The method according to claim 13, wherein the method comprises positioning a belted absorbent garment in a clearly marked initial position on the movable mechanical members, fastening the belted absorbent garment around the movable mechanical members by stretching the belt using a predetermined force, wrapping a crotch portion and body panels of the absorbent garment around the movable mechanical members and fastening the second body panel to the external surface of at least one of the belt sections, adding a predetermined weight to the belted absorbent garment, moving the movable mechanical members a predetermined distance apart and back at a predetermined speed a predetermined number of times, and recording the position of the belted absorbent product from its initial position a predetermined time after the final expansion and contraction cycle has been completed.

17. The method according to claim 13, wherein the method comprises providing a vertical scale in the vicinity of said movable members to determine the amount of downward slippage during the, or each expansion and contraction cycle.

18. The method according to claim 13, wherein the method comprises providing a manufactured belted absorbent garment or its packaging with information or a parameter that is indicative of how well said belted absorbent garment stays in place on a user's waist when in use.

19. An absorbent garment having a longitudinal and a transverse direction and comprising:

a first body panel; a second body panel and a crotch portion therebetween in the longitudinal direction, each of said first and second body panels having a waist portion, said absorbent garment further being provided with belt sections attached to the waist portion of the first body panel and being adapted to be wrapped around the waist of a user of the absorbent garment and fastened together by a first fastener, the second body panel at its waist portion being provided with a second fastener adapted to be fastened to at least one of the belt sections in such a way that the absorbent garment will assume a pant-like shape wherein at least one belt section comprises inelastic panels and at least one elastic panel that extends up to 25% of the length of the belt section in the transverse direction thereof, as measured in the initial non-elongated state of the belt section.

20. The absorbent garment according to claim 19, wherein the at least one elastic panel requires a force less than an equal to 15N to be elongated by at least 60%.

* * * * *